(12) United States Patent
Rao et al.

(10) Patent No.: US 7,285,691 B2
(45) Date of Patent: Oct. 23, 2007

(54) PROCESS FOR THE PREPARATION OF 1,1,1,3,3,3-HEXAFLUOROPROPANE AND AT LEAST ONE OF 1,1,1,2,3,3-HEXAFLUOROPROPANE AND 1,1,1,2,3,3,3-HEPTAFLUOROPROPANE

(75) Inventors: Velliyur Nott Mallikarjuna Rao, Wilmington, DE (US); Allen C. Sievert, Elkton, MD (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/572,625

(22) PCT Filed: Oct. 13, 2004

(86) PCT No.: PCT/US2004/034447

§ 371 (c)(1),
(2), (4) Date: Mar. 17, 2006

(87) PCT Pub. No.: WO2005/037742

PCT Pub. Date: Apr. 28, 2005

(65) Prior Publication Data

US 2006/0258890 A1    Nov. 16, 2006

Related U.S. Application Data

(60) Provisional application No. 60/511,355, filed on Oct. 14, 2003.

(51) Int. Cl.
*C07C 17/10* (2006.01)
*C07C 17/00* (2006.01)

(52) U.S. Cl. .................................. 570/176; 570/175

(58) Field of Classification Search ............ 570/175, 570/176
See application file for complete search history.

(56) References Cited

U.S. PATENT DOCUMENTS

| | | |
|---|---|---|
| 3,865,885 A | 2/1975 | Bruce, Jr. |
| 3,878,257 A | 4/1975 | Bruce, Jr. |
| 5,036,036 A | 7/1991 | Lerou |
| 5,057,634 A | 10/1991 | Webster et al. |
| 5,068,472 A | 11/1991 | Webster et al. |
| 5,281,568 A | 1/1994 | Scott et al. |
| 5,414,165 A | 5/1995 | Nappa et al. |
| 5,449,656 A | 9/1995 | Scott et al. |
| 5,545,774 A | 8/1996 | Rao |
| 5,623,092 A | 4/1997 | Scott et al. |
| 5,902,911 A | 5/1999 | Rao et al. |
| 6,066,769 A | 5/2000 | Nappa et al. |
| 6,291,730 B1 | 9/2001 | Baker et al. |
| 6,403,524 B2 | 6/2002 | Scott et al. |
| 6,540,933 B1 | 4/2003 | Sievert et al. |
| 2001/0011061 A1 | 8/2001 | Scott et al. |

FOREIGN PATENT DOCUMENTS

| | | |
|---|---|---|
| AU | A 94/80340 | 6/1995 |
| DE | 23 58 254 | 6/1975 |
| EP | 0 502 605 | 9/1992 |
| EP | 0 657 408 | 6/1995 |
| GB | 902590 | 8/1962 |
| GB | 2 275 924 | 9/1994 |
| WO | WO95/32935 | 12/1995 |
| WO | WO98/10862 | 3/1998 |
| WO | WO99/51553 | 10/1999 |
| WO | WO99/51556 | 10/1999 |
| WO | WO99/62851 | 12/1999 |
| WO | WO2005/037431 | 4/2005 |
| WO | WO2005/037743 | 4/2005 |
| WO | WO2005/037744 | 4/2005 |

OTHER PUBLICATIONS

U.S. Appl. No. 10/572,626, filed Oct. 13, 2004, Rao et al.
U.S. Appl. No. 10/572,627, filed Oct. 13, 2004, Rao et al.
U.S. Appl. No. 10/572,628, filed Oct. 13, 2004, Amos et al.

*Primary Examiner*—J. Parsa

(57) ABSTRACT

A process is disclosed for the manufacture of 1,1,1,3,3,3-hexafluoropropane (HFC-236fa) and at least one 1,1,1,2,3, 3-hexafluoropropane (HFC-236ea) and 1,1,1,2,3,3,3-heptafluoropropane (HFC-227ea). The process involves (a) reacting HF, $Cl_2$, and at least one halopropene of the formula $CX_3CCl=CX_2$ (where each X is independently F or Cl) to produce a product including both $CF_3CCl_2CF_3$ and $CF_3CClFCClF_2$; (b) reacting $CF_3CCl_2CF_3$ and $CF_3CClFCClF_2$ produced in (a) with hydrogen to produce a product comprising $CF_3CH_2CF_3$ and at least one compound selected from the group consisting of $CHF_2CHFCF_3$, and $CF_3CHFCF_3$; and (c) recovering from the product produced in (b), $CF_3CH_2CF_3$ and at least one compound selected from the group consisting of $CHF_2CHFCF_3$ and $CF_3CHFCF_3$. In (a), the $CF_3CCl_2CF_3$ and $CF_3CClFCClF_2$ are produced in the presence of a chlorofluorination catalyst including a $ZnCr_2O_4$/crystalline α-chromium oxide composition, a $ZnCr_2O_4$/crystalline α-chromium oxide composition which has been treated with a fluorinating agent, a zinc halide/α-chromium oxide composition and/or a zinc halide/α-chromium oxide composition which has been treated with a fluorinating agent.

11 Claims, No Drawings

US 7,285,691 B2

PROCESS FOR THE PREPARATION OF 1,1,1,3,3,3-HEXAFLUOROPROPANE AND AT LEAST ONE OF 1,1,1,2,3,3-HEXAFLUOROPROPANE AND 1,1,1,2,3,3,3-HEPTAFLUOROPROPANE

This application represents a national filing under 35 U.S.C. 371 of PCT International Application No. PCT/US2004/034447 filed Oct. 13, 2004, and claims priority benefit of U.S. application Ser. No. 60/511,355 filed Oct. 14, 2003.

FIELD OF THE INVENTION

This invention relates to the synthesis of 1,1,1,3,3,3-hexafluoropropane, 1,1,1,2,3,3-hexafluoropropane, and 1,1,1,2,3,3,3-heptafluoropropane.

BACKGROUND

A number of chlorine-containing halocarbons are considered to be detrimental toward the Earth's ozone layer. There is a world-wide effort to develop materials having lower ozone depletion potential that can serve as effective replacements. For example, the hydrofluorocarbon, 1,1,1,2-tetrafluoroethane (HFC-134a) is being used as a replacement for dichlorodifluoromethane (CFC-12) in refrigeration systems. There is a need for manufacturing processes that provide halogenated hydrocarbons that contain less chlorine or no chlorine. The production of hydrofluorocarbons (i.e., compounds containing only carbon, hydrogen and fluorine), has been the subject of considerable interest to provide environmentally desirable products for use as solvents, blowing agents, refrigerants, cleaning agents, aerosol propellants, heat transfer media, dielectrics, fire extinguishants and power cycle working fluids. For example, 1,1,1,3,3,3-hexafluoropropane has utility as a fire extinguishant and as a refrigerant, 1,1,1,2,3,3-hexafluoropropane has utility as a refrigerant, and 1,1,1,2,3,3,3-heptafluoropropane has utility as a fire extinguishant and as a propellant.

SUMMARY OF THE INVENTION

This invention provides a process for the manufacture of 1,1,1,3,3,3-hexafluoropropane (HFC-236fa) and at least one compound selected from the group consisting of 1,1,1,2,3,3-hexafluoropropane (HFC-236ea) and 1,1,1,2,3,3,3-heptafluoropropane (HFC-227ea). The process comprises (a) reacting HF, $Cl_2$, and at least one halopropene of the formula $CX_3CCl=CX_2$, wherein each X is independently selected from the group consisting of F and Cl, to produce a product comprising $CF_3CCl_2CF_3$ and $CF_3CClFCClF_2$, wherein said $CF_3CCl_2CF_3$ and $CF_3CClFCClF_2$ are produced in the presence of a chlorofluorination catalyst comprising at least one composition selected from the group consisting of (i) compositions comprising $ZnCr_2O_4$ and crystalline α-chromium oxide, (ii) compositions comprising a zinc halide and α-chromium oxide and (iii) compositions of (i) or (ii) which have been treated with a fluorinating agent (e.g., anhydrous hydrogen fluoride); (b) reacting $CF_3CCl_2CF_3$ and $CF_3CClFCClF_2$ produced in (a) with hydrogen, optionally in the presence of HF, to produce a product comprising $CF_3CH_2CF_3$ and at least one compound selected from the group consisting of $CHF_2CHFCF_3$, and $CF_3CHFCF_3$; and (c) recovering from the product produced in (b), $CF_3CH_2CF_3$ and at least one compound selected from the group consisting of $CHF_2CHFCF_3$ and $CF_3CHFCF_3$.

DETAILED DESCRIPTION

This invention provides a process for the preparation of $CF_3CH_2CF_3$ (HFC-236fa) and $CF_3CHFCHF_2$ (HFC-236ea). This invention also provides a process for the preparation of HFC-236fa and $CF_3CHFCF_3$ (HFC-227ea).

In step (a) of the process of this invention, one or more halopropene compounds $CX_3CCl=CX_2$, wherein each X is independently selected from the group consisting of F and Cl, are reacted with chlorine ($Cl_2$) and hydrogen fluoride (HF) to produce a product mixture comprising $CF_3CCl_2CF_3$ (CFC-216aa) and $CF_3CClFCClF_2$ (CFC-216ba). Accordingly, this invention provides a process for the preparation of mixtures of $CF_3CCl_2CF_3$ (CFC-216aa) and $CF_3CClFCClF_2$ (CFC-216ba) from readily available starting materials.

Suitable starting materials for the process of this invention include $CF_3CCl=CF_2$ (CFC-1215xc), E— and Z—$CF_3CCl=CClF$ (CFC-1214xb), $CF_3CCl=CCl_2$ (CFC-1213xa), $CClF_2CCl=CCl_2$ (CFC-1212xa), $CCl_2FCCl=CCl_2$ (CFC-1211xa), and $CCl_3CCl=CCl_2$ (hexachloropropene, HCP) or mixtures thereof.

Preferred starting materials for the process of this invention are $CF_3CCl=CCl_2$ (CFC-1213xa) and $CCl_3CCl=CCl_2$ (hexachloropropene, HCP) based on their ready accessibility.

Preferably, the reaction of HF and $Cl_2$ with halopropenes $CX_3CCl=CX_2$ is carried out in the vapor phase in a heated tubular reactor. A number of reactor configurations are possible including horizontal or vertical orientation of the reactor and different modes of contacting the halopropene starting materials with HF and chlorine. Preferably the HF and chlorine are substantially anhydrous.

In one embodiment of step (a) the halopropene starting material(s) are fed to the reactor containing the chlorofluorination catalyst. The halopropene starting material(s) may be initially vaporized and fed to the reactor as gas(es).

In another embodiment of step (a), the halopropene starting material(s) may be contacted with HF in a pre-reactor. The pre-reactor may be empty (i.e., unpacked), but is preferably filled with a suitable packing such as Monel™ or Hastelloy™ nickel alloy turnings or wool, or other material inert to HCl and HF which allows efficient mixing of $CX_3CCl=CX_2$ and HF vapor.

When liquid feed of the halopropene starting material(s) to the pre-reactor is used, it is preferable for the pre-reactor to be oriented vertically with $CX_3CCl=CX_2$ entering the top of the reactor and pre-heated HF vapor introduced at the bottom of the reactor.

Suitable temperatures for the pre-reactor are within the range of from about 80° C. to about 250° C., preferably from about 100° C. to about 200° C. Under these conditions, for example, hexachloropropene is converted to a mixture containing predominantly CFC-1213xa. The starting material feed rate is determined by the length and diameter of the reactor, the temperature, and the degree of fluorination desired within the pre-reactor. Slower feed rates at a given temperature will increase contact time and tend to increase the amount of conversion of the starting material and increase the degree of fluorination of the products.

The term "degree of fluorination" means the extent to which fluorine atoms replace chlorine substituents in the $CX_3CCl=CX_2$ starting materials. For example, $CF_3CCl=CClF$ represents a higher degree of fluorination than $CClF_2CCl=CCl_2$ and $CF_3CCl_2CF_3$ represents a higher degree of fluorination than $CClF_2CCl_2CF_3$.

The molar ratio of HF fed to the pre-reactor, or otherwise to the reaction zone of step (a), to halopropene starting material fed in step (a), is typically from about stoichiometric to about 50:1. The stoichiometric ratio depends on the average degree of fluorination of the halopropene starting material(s) and is typically based on formation of $C_3Cl_2F_6$. For example, if the halopropene is HCP, the stoichiometric ratio of HF to HCP is 6:1; if the halopropene is CFC-1213xa, the stoichiometric ratio of HF to CFC-1213xa is 3:1. Preferably, the ratio of HF to halopropene starting material is from about twice the stoichiometric ratio of HF to halopropene (based on formation of $C_3Cl_2F_6$) to about 30:1. Higher ratios of HF to halopropene are not particularly beneficial; lower ratios result in reduced yields of $C_3Cl_2F_6$.

If the halopropene starting materials are contacted with HF in a pre-reactor, the effluent from the pre-reactor is contacted with chlorine in the reaction zone of step (a).

In another embodiment of the invention, the halopropene starting material(s) may be contacted with $Cl_2$ and HF in a pre-reactor. The pre-reactor may be empty (i.e., unpacked), but is preferably filled with a suitable packing such as Monel™ or Hastelloy™ nickel alloy turnings or wool, activated carbon, or other material inert to HCl, HF, and $Cl_2$ which allows efficient mixing of $CX_3CCl$=$CX_2$, HF, and $Cl_2$.

Typically at least a portion of the halopropene starting material(s) react(s) with $Cl_2$ and HF in the pre-reactor by addition of $Cl_2$ to the olefinic bond to give a saturated halopropane as well as by substitution of at least a portion of the Cl substituents in the halopropropane and/or halopropene by F. Suitable temperatures for the pre-reactor in this embodiment of the invention are within the range of from about 80° C. to about 250° C., preferably from about 100° C. to about 200° C. Higher temperatures result in greater conversion of the halopropene(s) entering the reactor to saturated products and a greater degree of halogenation of the starting material. In the presence of HF, the degree of fluorination will also increase at higher pre-reactor temperatures.

The term "degree of halogenation" means the extent to which hydrogen substituents in a halocarbon have been replaced by halogen and carbon-carbon double bonds have been saturated with halogen. For example, $CF_3CCl_2CClF_2$ has a higher degree of halogenation than $CF_3CCl$=$CCl_2$. Also, $CF_3CClFCF_3$ has a higher degree of halogenation than $CF_3CHClCF_3$.

The molar ratio of $Cl_2$ fed to the pre-reactor, or otherwise to the reaction zone of step (a), to halopropene starting material(s) fed in step (a), is typically from about 1:1 to about 10:1. Feeding $Cl_2$ at less than a 1:1 ratio will result in the presence of relatively large amounts of unsaturated materials and hydrogen-containing side products in the reactor effluent.

In a preferred embodiment of step (a), the halopropene starting materials are vaporized, preferably in the presence of HF, and contacted with HF and $Cl_2$ in a pre-reactor and then contacted with the chlorofluorination catalyst. If the preferred amounts of HF and $Cl_2$ are fed in the pre-reactor, additional HF and $Cl_2$ are not required in the reaction zone.

Suitable temperatures in the reaction zone(s) of step (a) are within the range of from about 230° C. to not more than 425° C., preferably from about 250° C. to about 400° C. Higher temperatures result in greater conversion of the $CX_3CCl$=$CX_2$ starting materials, but also result in formation of overfluorinated products such as $CF_3CClFCF_3$ and contribute to reduced catalyst life. As illustrated in the Examples, the preferred temperature range is somewhat dependent on the activity of the catalyst. Temperatures lower than about 250° C. result in low yields of CFC-216aa and CFC-216ba. Unconverted starting materials and products having a degree of fluorination lower than six may be recycled back to the reaction zone.

Suitable reactor pressures for vapor phase embodiments of this invention may be in the range of from about 1 to about 30 atmospheres. Reactor pressures of about 5 atmospheres to about 20 atmospheres may be advantageously employed to facilitate separation of HCl from other reaction products in step (b) of the process.

The chlorofluorination catalysts which are used in the process of the present invention are preferably compositions comprising $ZnCr_2O_4$ (zinc chromite) and crystalline α-$Cr_2O_3$ (α-chromium oxide) or compositions obtained by treatment of said compositions comprising $ZnCr_2O_4$ (zinc chromite) and crystalline α-$Cr_2O_3$ (α-chromium oxide) with a fluorinating agent. The amount of zinc relative to the total of chromium and zinc in these compositions is preferably from about 1 atom % to about 25 atom %.

Of note are chromium-containing catalyst compositions comprising $ZnCr_2O_4$ (zinc chromite) and crystalline α-chromium oxide wherein the $ZnCr_2O_4$ contains between about 10 atom percent and 67 atom percent of the chromium in the composition and at least about 70 atom percent of the zinc in the composition, and wherein at least about 90 atom percent of the chromium present as chromium oxide in the composition is present as $ZnCr_2O_4$ or crystalline α-chromium oxide; and also of note are chromium-containing catalyst compositions, prepared by treatment of such compositions comprising $ZnCr_2O_4$ and crystalline α-chromium oxide with a fluorinating agent. Also of note are such chromium-containing catalyst compositions which comprise $ZnCr_2O_4$ and crystalline α-chromium oxide wherein the $ZnCr_2O_4$ contains between about 20 atom percent and about 50 atom percent of the chromium in the composition. Also of note are such chromium-containing catalyst compositions which comprise $ZnCr_2O_4$ and crystalline α-chromium oxide wherein the $ZnCr_2O_4$ contains at least about 90 atom percent of the zinc in the composition. Also of note are such chromium-containing catalyst compositions comprising zinc chromite and crystalline α-chromium oxide wherein greater than 95 atom percent of the chromium that is not present as zinc chromite is present as crystalline α-chromium oxide. Also of note are such chromium-containing catalyst compositions which consist essentially of $ZnCr_2O_4$ (zinc chromite) and crystalline α-chromium oxide.

These compositions may be prepared, for example, by co-precipitation methods followed by calcination.

In a typical co-precipitation procedure, an aqueous solution of zinc and chromium(III) salts is prepared. The relative concentrations of the zinc and chromium(III) salts in the said aqueous solution is dictated by the bulk atom percent zinc relative to chromium desired in the final catalyst. The concentration of chromium(III) in the aqueous solution is typically in the range of 0.3 to 3 moles per liter with 0.75-1.5 moles per liter being a preferred concentration. While different chromium(III) salts might be employed, chromium (III) nitrate or its hydrated forms such as $[Cr(NO_3)_3(H_2O)_9]$, are the most preferred chromium(ill) salts for preparation of said aqueous solution.

While different zinc salts might be employed for preparation of said aqueous solutions, preferred zinc salts for preparation of catalysts for the process of this invention include zinc(II) nitrate and its hydrated forms such as $[Zn(NO_3)_2(H_2O)_6]$.

The aqueous solution of the chromium(III) and zinc salts may then be evaporated either under vacuum or at elevated temperature to give a solid which is then calcined.

It is preferred to treat the aqueous solution of the chromium(III) and zinc salts is treated with a base such as ammonium hydroxide (aqueous ammonia) to precipitate the zinc and chromium as the hydroxides. Bases containing alkali metals such as sodium or potassium hydroxide or the carbonates may be used but are not preferred. The addition of ammonia to the aqueous solution of the chromium(III) and zinc salt is typically carried out gradually over a period of 1 to 12 hours. The pH of the solution is monitored during the addition of base. The final pH is typically in the range of 6.0 to 11.0, preferably from about 7.5 to about 9.0, most preferably about 8.0 to 8.7. The precipitation of the zinc and chromium hydroxide mixture is typically carried out at a temperature of about 15° C. to about 60° C., preferably from about 20° C. to about 40° C. After the ammonia is added, the mixture is typically stirred for up to 24 hours. The precipitated chromium and zinc hydroxides serve as precursors to $ZnCr_2O_4$ and α-chromium oxide.

After the precipitation of the zinc and chromium hydroxide mixture is complete, the mixture is dried by evaporation. This may be carried out by heating the mixture in an open pan on a hot plate or steam bath or in an oven or furnace at a suitable temperature. Suitable temperatures include temperatures from about 60° C. to about 130° C. (for example, about 100° C. to about 120° C.). Alternatively the drying step may be carried out under vacuum using, for example, a rotary evaporator.

Optionally, the precipitated zinc and chromium hydroxide mixture may be collected and, if desired, washed with deionized water. Preferably the precipitated zinc and chromium hydroxide mixture is not washed prior to the drying step.

After the water has been removed from the zinc and chromium hydroxide mixture, the nitrate salts are then decomposed by heating the solid from about 250° C. to about 350° C. The resulting solid is then calcined at temperatures of from about 400° C. to about 1000° C., preferably from about 400° C. to about 900° C.

Further information on the zinc and chromium compositions useful for this invention is provided in U.S. patent application Ser. No. 60/511,353 [CL2244 US PRV] filed Oct. 14, 2003, and hereby incorporated by reference herein in its entirety (see also corresponding International Application No. PCT/US2004/034446).

The calcined zinc chromite/α-chromium oxide compositions of the present invention may be pressed into various shapes such as pellets for use in packing reactors. It may also be used in powder form.

Typically, the calcined compositions will be pre-treated with a fluorinating agent prior to use as catalysts for changing the fluorine content of halogenated carbon compounds. Typically this fluorinating agent is HF though other materials may be used such as sulfur tetrafluoride, carbonyl fluoride, and fluorinated carbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the catalyst in a suitable container which can be the reactor to be used to perform the process in the instant invention, and thereafter, passing HF over the dried, calcined catalyst so as to partially saturate the catalyst with HF. This is conveniently carried out by passing HF over the catalyst for a period of time, for example, about 0.1 to about 10 h at a temperature of, for example, about 200° C. to about 450° C. Nevertheless, this pretreatment is not essential.

Other catalysts suitable for the chlorofluorinations of step (a) are compositions comprising a zinc halide and α-chromium oxide and compositions obtained by treatment of said compositions comprising a zinc halide and α-chromium oxide with a fluorinating agent. U.S. Pat. No. 3,878,257 discloses an example of such catalysts. The amount of zinc relative to the total of chromium and zinc in these compositions is preferably from about 0.1 atom % to about 25 atom %; and is more preferably from about 2 atom % to about 10 atom %. Of note are compositions wherein a zinc halide is supported on a support comprising α-chromium oxide. Preferably, the α-chromium oxide is prepared according to U.S. Pat. No. 5,036,036. Pretreatment with a fluorinating agent can be carried out as indicated above for the calcined zinc chromite/α-chromium oxide compositions.

Compounds that are produced in the chlorofluorination process in step (a) include the halopropanes $CF_3CCl_2CF_3$ (CFC-216aa) and $CF_3CClFCClF_2$ (CFC-216ba).

Halopropane by-products that have a higher degree of fluorination than CFC-216aa and CFC-216ba that may be produced in step (a) include $CF_3CClFCF_3$ (CFC-217ba) and $CF_3CF_2CF_3$ (FC-218).

Halopropane and halopropene by-products that may be formed in step (a) which have lower degrees of fluorination and/or halogenation than CFC-216aa and CFC-216ba include $CF_3CCl_2CClF_2$ (CFC-215aa), $CF_3CClFCCl_2F$ (CFC-215bb), $CF_3CCl_2CCl_2F$ (CFC-214ab), and $CF_3CCl=CF_2$ (CFC-1215xc).

Prior to step (b), $CF_3CCl_2CF_3$, $CF_3CClFCClF_2$, (and optionally HF) from the effluent from the reaction zone in step (a), are typically separated from the low boiling components of the effluent (which typically comprise HCl, $Cl_2$, HF, and over-fluorinated products such as $CF_3CClFCF_3$) and the under-fluorinated components of the effluent (which typically comprise $C_3Cl_3F_5$ isomers, $C_3Cl_4F_4$ isomers, and/or under-halogenated components such as $C_3Cl_2F_4$ isomers and $CF_3CCl=CCl_2$). The higher boiling components may be returned to step (a).

In one embodiment of this invention, the under-fluorinated components include CFC-215aa and CFC-215bb, which are converted to $CF_3CH_2CHF_2$ (HFC-245fa) and $CF_3CHFCH_2F$ (HFC-245eb) as disclosed in U.S. patent application Ser. No. 60/511,284 [CL2320 US PRV] filed Oct. 14, 2003 (see also corresponding International Application No. PCT/US2004/034454).

In another embodiment of this invention, the reactor effluent from step (a) is delivered to a distillation column in which HCl and any HCl azeotropes are removed from the top of the column while the higher boiling components are removed from the bottom of the column. The products recovered from the bottom of the first distillation column are then delivered to a second distillation column in which HF, $Cl_2$, and any CFC-217ba are recovered at the top of the second distillation column and remaining HF and organic products, comprising $CF_3CCl_2CF_3$ and $CF_3CClFCClF_2$, are recovered at the bottom of the distillation column. The products recovered from the bottom of the second distillation column may be delivered to further distillation columns or may be delivered to a decanter controlled at a suitable temperature to permit separation of an organic-rich phase and an HF-rich phase. The HF-rich phase may be distilled to recover HF which is then recycled to step (a). The organic-rich phase may then be delivered to step (b).

In another embodiment of this invention, the CFC-217ba recovered as an over-fluorinated by-product may be converted to hexafluoropropene (HFP) as disclosed in U.S. Pat. Nos. 5,068,472 and 5,057,634.

In step (b) of the process, $CF_3CCl_2CF_3$ and $CF_3CClFCClF_2$ are contacted with hydrogen ($H_2$) in a second reaction zone. The $CF_3CCl_2CF_3$ and $CF_3CClFCClF_2$ may be fed to the reactor zone at least in part as their azeotropes with HF.

In one embodiment of step (b), a mixture comprising $CF_3CCl_2CF_3$ and $CF_3CClFCClF_2$ is delivered in the vapor phase, along with hydrogen, to a reactor fabricated from nickel, iron, titanium, or their alloys, as described in U.S. Pat. No. 6,540,933; the teachings of this disclosure are incorporated herein by reference. A reaction vessel of these materials (e.g., a metal tube) optionally packed with the metal in suitable form may also be used. When reference is made to alloys, it is meant a nickel alloy containing form 1 to 99.9% (by weight) nickel, an iron alloy containing 0.2 to 99.8% (by weight) iron, and a titanium alloy containing 72-99.8% (by weight) titanium. Of note is use of an empty (unpacked) reaction vessel made of nickel or alloys of nickel such as those containing 40% to 80% nickel, e.g., Inconel™ 600 nickel alloy, Hastelloy™ C617 nickel alloy, or Hastelloy™ C276 nickel alloy.

When used for packing, the metal or metal alloys may be particles or formed shapes such as perforated plates, rings, wire, screen, chips, pipe, shot, gauze, or wool.

The temperature of the reaction in this embodiment of step (b) can be between about 350° C. to about 600° C., and is preferably at least about 450° C.

The molar ratio of hydrogen to the CFC-216aa/CFC-216ba mixture fed to the reaction zone should be in the range of about 0.1 mole $H_2$ per mole of CFC-216 isomer to about 60 moles of $H_2$ per mole of CFC-216 isomer, more preferably from about 0.4 to 10 moles of $H_2$ per mole of CFC-216 isomer. The higher the ratio of $H_2$ to CFC-216 isomer, the more $CF_3CHFCHF_2$ that is formed.

Alternatively, the contacting of hydrogen with the mixture of CFC-216aa and CFC-216ba, and optionally HF, is carried out in the presence of a hydrogenation catalyst. In this embodiment of step (b), said mixture is delivered in the vapor phase, along with hydrogen, to the reaction zone containing a hydrogenation catalyst. Hydrogenation catalysts suitable for use in this embodiment include catalysts comprising at least one metal selected from the group consisting of rhenium, iron, ruthenium, osmium, cobalt, rhodium, iridium, nickel, palladium, and platinum. Said catalytic metal component is typically supported on a carrier such as carbon or graphite or a metal oxide, fluorinated metal oxide, or metal fluoride where the carrier metal is selected from the group consisting of magnesium, aluminum, titanium, vanadium, chromium, iron, and lanthanum.

The supported metal catalysts may be prepared by conventional methods known in the art such as by impregnation of the carrier with a soluble salt of the catalytic metal (e.g., palladium chloride or rhodium nitrate) as described by Satterfield on page 95 of *Heterogenous Catalysis in Industrial Practice*, $2^{nd}$ edition (McGraw-Hill, New York, 1991). The concentration of the catalytic metal(s) on the support is typically in the range of about 0.1% by weight of the catalyst to about 5% by weight.

Suitable temperatures for the reaction zone containing said hydrogenation catalyst are in the range of from about 110° C. to about 400° C., preferably from about 125° C. to about 350° C. Higher temperatures typically result in greater conversion of CFC-216aa and CFC-216ba with fewer partially chlorinated intermediates such as $C_3HClF_6$ isomers. At reaction zone temperatures in the range of 125° C. to 300° C. the primary products of the hydrodechlorination process are HFC-236fa and HFC-236ea with the amount of HFC-236ea increasing as the temperature is increased due to higher conversion of $CF_3CClFCClF_2$ and the intermediate compounds $CF_3CClFCHF_3$ (HCFC-226ba) and $CF_3CHFCClF_2$ (HCFC-226ea).

Temperatures above about 400° C. may cause hydrogenolysis of carbon-fluorine and carbon-carbon bonds; temperatures lower than about 125° C. will result in low conversion of the halopropanes and the formation of large amounts of partially chlorinated intermediates.

The amount of hydrogen ($H_2$) fed to the reaction zone containing said hydrogenation catalyst is typically from about 1 mole of $H_2$ per mole of dichlorohexafluoropropane to about 20 moles of $H_2$ per mole of dichlorohexafluoropropane, preferably from about 2 moles of $H_2$ per mole of dichlorohexafluoropropane to about 10 moles of $H_2$ per mole of dichlorohexafluoropropane.

The pressure used in the step (b) reaction zone is not critical and may be in the range of from about 1 to 30 atmospheres. A pressure of about 20 atmospheres may be advantageously employed to facilitate separation of HCl from other reaction products.

To facilitate production of HFC-227ea in step (b), anhydrous hydrogen fluoride (HF) may be-co-fed to the reaction zone containing a hydrogenation catalyst. The amount of HF co-fed along with hydrogen to the reaction zone may be from about 0.2 mole HF per mole of CFC-216 isomer to about 4 moles of HF per mole of CFC-216 isomer. Under these conditions it is possible to obtain a mixture of products containing predominantly HFC-236fa and HFC-236ea or a mixture of products containing predominantly HFC-236fa and HFC-227ea by changing the temperature of the reaction zone. At temperatures in the reaction zone of 125° C. to about 250° C., the product mixture contains predominantly HFC-236fa and HFC-236ea. At temperatures in the reaction zone of about 275° C. to about 350° C., the product mixture contains predominantly HFC-236fa and HFC-227ea. Thus, the content of the product mixture is adjustable by manipulation of $C_3Cl_2F_6$/HF/$H_2$ feed ratio and reaction zone temperature.

The effluent from the step (b) reaction zone typically includes HCl, unreacted hydrogen, $CF_3CF=CF_2$ (HFP), $CF_3CH_2CF_3$ (HFC-236fa), $CF_3CHFCHF_2$ (HFC-236ea), and $CF_3CHFCF_3$ (HFC-227ea), as well as any HF carried over from step (a) or step (b). In addition, small amounts of $CF_3CF_2CH_2F$ (HFC-236cb), $CF_3CCl=CF_2$ (CFC-1215xc), and partially chlorinated by-products such as $C_3HClF_6$ isomers including $CF_3CHClCF_3$ (HCFC-226da), $CF_3CClFCHF_3$ (HCFC-226ba), $CF_3CHFCClF_2$ (HCFC-226ea), may be formed.

In step (c), the desired products are recovered. The reactor effluent from step (b) may be delivered to a separation unit to recover $CF_3CH_2CF_3$, and $CF_3CHFCHF_2$, and/or $CF_3CHFCF_3$, individually, as a mixture, or as their HF azeotropes.

The partially chlorinated by-products, including any unconverted CFC-216ba and CFC-216aa, may be recovered and returned to step (a) or returned to the hydrogenation reactor in step (b). The hexafluoropropene may recovered separately or returned to steps (a) or (b).

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The following specific embodiments are to be construed as merely illustrative, and do not constrain the remainder of the disclosure in any way whatsoever.

EXAMPLES

| LEGEND | |
|---|---|
| 214ab is $CF_3CCl_2CCl_2F$ | 215aa is $CF_3CCl_2CClF_2$ |
| 215bb is $CCl_2FCClFCF_3$ | 216aa is $CF_3CCl_2CF_3$ |
| 216ba is $CClF_2CClFCF_3$ | 217ba is $CF_3CClFCF_3$ |
| 226ba is $CF_3CClFCHF_2$ | 226da is $CF_3CHClCF_3$ |
| 226ea is $CF_3CHFCClF_2$ | 227ea is $CF_3CHFCF_3$ |
| 236cb is $CF_3CF_2CH_2F$ | 236ea is $CF_3CHFCHF_2$ |
| 236fa is $CF_3CH_2CF_3$ | 245cb is $CH_3CF_2CF_3$ |
| 254eb is $CH_3CHFCF_3$ | 1213xa is $CF_3CCl=CCl_2$ |
| 1215xc is $CF_3CCl=CF_2$ | 1225 is $C_3HF_5$ |
| 1234 is $C_3H_2F_4$ | HFP is $CF_2=CFCF_3$ |

Catalyst Preparation

Comparative Preparation Example 1

Preparation of 100% Chromium Catalyst (400° C.)

A solution of 400 g $Cr(NO_3)_3[9(H_2O)]$ (1.0 mole) in 1000 mL of deionized water was treated dropwise with 477 mL of 7.4M aqueous ammonia raising the pH to about 8.5. The slurry was stirred at room temperature overnight. After re-adjusting the pH to 8.5 with ammonia, the mixture was poured into evaporating dishes and dried in air at 120° C. The dried solid was then calcined in air at 400° C.; the resulting solid weighed 61.15 g. The catalyst was pelletized (−12 to +20 mesh, (1.68 to 0.84 mm)) and 28.2 g (20 mL) was used in Comparative Example 3.

Comparative Preparation Example 2

Preparation of 2% Zinc on Alumina Catalyst

Aluminum oxide (4.90 moles, Harshaw 3945, dried at 110° C.) was added to a solution of 20.85 g $ZnCl_2$ (0.153 mole) dissolved in 460 mL of distilled water. Water was evaporated from the mixture with stirring and then dried at 110° C. for three days. The catalyst was pelletized (−12 to +20 mesh, (1.68 to 0.84 mm)) and 21.1 g (30 mL) was used in Comparative Example 1.

Preparation Example 1

Preparation of 2% Zinc Chloride Supported on Chromium Oxide

A solution of 1.20 g $ZnCl_2$ (8.81 mmoles) in 60 mL of deionized water contained in a 125 mm×65 mm glass dish was treated with 60.00 g (0.357 mole) of 12-20 mesh $Cr_2O_3$. The dish was placed on a warm hot plate and the slurry allowed to dry with occasional stirring. The resulting solid was then dried overnight at 130° C.; the resulting solid weighed 60.42 g. The catalyst was pelletized (−12 to +20 mesh, (1.68 to 0.84 mm)) and 41.5 g (30 mL) was used in Example 10.

Preparation Example 2

Preparation of 95% Chromium/5% Zinc Catalyst (450° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 450° C. for 20 hours; the resulting solid weighed 76.72 g. The catalyst was pelletized (−12 to +20 mesh, (1.68 to 0.84 mm)) and 38.5 g (25 mL) was used in Example 11.

Preparation Example 3

Preparation of 90% Chromium/10% Zinc Catalyst (900° C.)

A solution of 360.13 g $Cr(NO_3)_3[9(H_2O)]$ (0.900 mole) and 29.75 g $Zn(NO_3)_2[6(H_2O)]$ (0.100 mole) was prepared in 1000 mL of deionized water. The solution was treated with 450 mL of 7.4M aqueous ammonium hydroxide over the course of 1.4 hours; the pH increased from 1.9 to pH 8.4. The slurry was stirred at room temperature overnight and then dried at 120° C. in the presence of air. The dried solid was then calcined in air at 900° C. for 20 hours; the resulting solid weighed 75.42 g. The catalyst was pelletized (−12 to +20 mesh, (1.68 to 0.84 mm)) and 42.3 g (25 mL) was used in Examples 5 and 6.

Preparation Example 4

Preparation of 95% Chromium/5% Zinc Catalyst (900° C.)

A solution of 380.14 g $Cr(NO_3)_3[9(H_2O)]$ (0.950 mole) and 14.87 g $Zn(NO_3)_2[6(H_2O)]$ (0.050 mole) was prepared in 1000 mL of deionized water. The solution was treated with 450 mL of 7.4M aqueous ammonium hydroxide over the course of one hour; the pH increased from 1.7 to pH 8.4. The slurry was stirred at room temperature overnight and then dried at 120° C. in an oven in the presence of air. The dried solid was then calcined in air at 900° C. for 20 hours; the resulting solid weighed 70.06 g. The catalyst was pelletized (−12 to +20 mesh, (1.68 to 0.84 mm)) and 25.3 g (14 mL) was used in Examples 1 and 2.

Preparation Example 5

Preparation of 98% Chromium/2% Zinc Catalyst (900° C.)

A solution of 392.15 g $Cr(NO_3)_3[9(H_2O)]$ (0.980 mole) and 5.94 g $Zn(NO_3)_2[6(H_2O)]$ (0.020 mole) was prepared in 1000 mL of deionized water. The solution was treated with 450 mL of 7.4M aqueous ammonium hydroxide over the course of 0.58 hour; the pH increased from 1.67 to pH 8.35. The slurry was stirred at room temperature overnight and then dried at 120° C. in an oven in the presence of air. The dried solid was then calcined in air at 900° C. for 21 hours; the resulting solid weighed 66.00 g. The catalyst was pelletized (−12 to +20 mesh, (1.68 to 0.84 mm)) and 44.9 g (23 mL) was used in Example 7.

Preparation Example 6

Preparation of 10% Zinc Chloride Supported on Chromium Oxide

A solution of 6.0 g $ZnCl_2$ (44 mmoles) in 300 mL of deionized water contained in a 170 mm×90 mm glass dish was treated with 60.00 g (0.357 mole) of 12-20 mesh $Cr_2O_3$. The dish was placed on a warm hot plate and the slurry allowed to dry with occasional stirring. The resulting solid was then dried overnight at 130° C.; the resulting solid weighed 65.02 g. The catalyst was pelletized (−12 to +20 mesh, (1.68 to 0.84 mm)) and 37.5 g (25 mL) was used in Example 8.

Preparation Example 7

Preparation of 98.1% Chromium/1.9% Zinc Catalyst (550° C.)

A solution of 516.46 g $Cr(NO_3)_3[9(H_2O)]$ (1.29 moles) and 7.31 g $Zn(NO_3)_2[6(H_2O)]$ (0.0246 mole) was prepared in 500 mL of distilled water in 1L beaker resting on a hot plate. The mixture was then transferred to a Pyrex™ container and the container placed in a furnace. The container was heated from room temperature to 125° C. at 10° C./min and then held at 125° C. for six hours. The container was heated from 125° C. to 350° C. at 1° C./min and then held at 350° C. for six hours. The container was heated from 350° C. to 550° C. at 1° C./min and then held at 550° C. for 24 hours. The catalyst was pelletized (−12 to +20 mesh, (1.68 to 0.84 mm)) and 29.9 g (20 mL) was used in Example 9.

Preparation Example 8

Preparation of 80% Chromium/20% Zinc Catalyst (900° C.)

A solution of 320.12 g of $Cr(NO_3)_3[9(H_2O)]$ (0.800 mole) and 59.49 g $Zn(NO_3)_2[6(H_2O)]$ (0.200 mole) was prepared in 1000 mL of deionized water. The solution was treated with 450 mL of 7.4M aqueous ammonium hydroxide over the course of one hour; the pH increased from about 1.7 to about pH 8.4. The slurry was stirred at room temperature overnight and then dried at 120° C. in an oven in the presence of air. The dried solid was then calcined in air at 900° C. for 22 hours; the resulting solid weighed 75.80 g. The catalyst was pelletized (−12 to +20 mesh, (1.68 to 0.84 mm)) and 41.7 g (25 mL) was used in Examples 3 and 4.

Examples 1-11 and Comparative Examples 1-4

General Procedure for Chlorofluorination of $CF_3CCl=CCl_2$

A weighed quantity of pelletized catalyst was placed in a ⅝" (1.58 cm) diameter Inconel™ nickel alloy reactor tube heated in a fluidized sand bath. The tube was heated from 50° C. to 175° C. in a flow of nitrogen (50 cc/min; 8.3 $(10)^{-7} m^3$/sec) over the course of about one hour. HF was then admitted to the reactor at a flow rate of 50 cc/min $(8.3(10)^{-7} m^3$/sec). After 0.5 to 2 hours the nitrogen flow was decreased to 20 cc/min $(3.3(10)^{-7} m^3$/sec) and the HF flow increased to 80 cc/min $(1.3(10)^{-6} m^3$/sec); this flow was maintained for about 1 hour. The reactor temperature was then gradually increased to 400° C. over 3 to 5 hours. At the end of this period, the HF flow was stopped and the reactor cooled to 300° C. under 20 sccm $(3.3(10)^{-7} m^3$/sec) nitrogen flow. CFC-1213xa was fed from a pump to a vaporizer maintained at about 118° C. The CFC-213xa vapor was combined with the appropriate molar ratios of HF and $Cl_2$ in a 0.5 inch (1.27 cm) diameter Monel™ nickel alloy tube packed with Monel™ turnings. The mixture of reactants then entered the reactor; the contact time was 30 seconds unless otherwise indicated. All reactions were conducted at a nominal pressure of one atmosphere. The results of CFC-1213xa chlorofluorination over the several catalysts are shown in Table 1; analytical data is given in units of GC area %.

Examples 12-18

Hydrodechlorination of a $CF_3CCl_2CF_3$(49.7%)/ $CClF_2CClFCF_3$(50.3%) Mixture The results of the hydrodechlorination of a mixture of $CF_3CCl_2CF_3$ and $CF_3CClF_2CClF_2$ over a commercial 1% Pd supported on fluorided alumina catalyst are shown in Table 2. The product analytical data is given in units of GC area %. The nominal catalyst bed volume was 15 mL; the contact time was 30 seconds. Prior to beginning the hydrodechlorination, the catalyst was activated by treatment with 20 sccm air at 400° C. for two hours. The catalyst was then reduced in a stream of 25 sccm hydrogen at 150-200° C. for 2.2 hours followed by treatment with a mixture of HF (80 sccm) and nitrogen (20 sccm) at 200-400° C. for 3.5 hours. The catalyst was then purged with nitrogen at 200C. The CFC-216aa/216ba mixture was fed from a pump to a vaporizer maintained at about 65-70° C. The CFC-216 vapor was combined with the appropriate molar ratios of HF in a 0.5 inch (1.27 cm) diameter Monel™ nickel alloy tube packed with Monel™ turnings. The mixture of reactants then entered the reactor; the contact time was 30 seconds unless otherwise indicated. All reactions were conducted at a nominal pressure of one atmosphere.

TABLE 1

| EX. NO. | HF:1213:$Cl_2$ | T ° C. | Catalyst | 1215xc | 217ba | 226da | 216aa | 216ba | 215aa | 215bb | 214ab |
|---|---|---|---|---|---|---|---|---|---|---|---|
| 1 | 30:1:10 | 280 | Cr/Zn 95/5 900° C. | 0.03 | 4.7 | 0.1 | 7.2 | 13.1 | 42.6 | 27.1 | 3.3 |
| 2 | 30:1:10 | 320 | Cr/Zn 95/5 900° C. | 0.05 | 7.5 | 0.2 | 16.2 | 18.4 | 33.5 | 21.7 | 0.5 |
| 3 | 20:1:4 | 280 | Cr/Zn 80/20 900° C. | 1.6 | 0.3 | 0.4 | 11.0 | 10.5 | 34.8 | 38.6 | 1.0 |
| 4 | 20:1:4 | 380 | Cr/Zn 80/20 900° C. | 0.4 | 3.6 | 0.2 | 35.9 | 39.2 | 18.2 | 0 | 0 |
| 5 | 20:1:4 | 300 | Cr/Zn 90/10 900° C. | 0.3 | 0.6 | 1.0 | 21.8 | 8.6 | 52.4 | 13.8 | 0.2 |
| 6 | 30:1:10 | 300 | Cr/Zn 90/10 900° C. | 0.1 | 0.8 | 0.5 | 16.9 | 10.3 | 54.9 | 15.2 | 0.2 |
| 7 | 20:1:4 | 330 | Cr/Zn 98/2 900° C. | 0.1 | 11.2 | 0.5 | 28.0 | 22.7 | 28.9 | 6.6 | 0.03 |
| 8 | 20:1:4 | 320 | Cr/$ZnCl_2$ 10% | 0.3 | 20.2 | 0.1 | 10.8 | 3.9 | 47.4 | 26.0 | 9.5 |
| 9[a] | 20:1:4 | 300 | Cr/Zn 98/2 550° C. | 1.6 | 16.8 | 1.3 | 24.1 | 10.2 | 39.2 | 14.8 | 0.5 |
| 10 | 20:1:4 | 280 | Cr/$ZnCl_2$ 2% | 0.4 | 3.1 | 0.9 | 16.0 | 14.1 | 62.6 | 1.6 | — |
| 11 | 20:1:4 | 320 | Cr/Zn 95/5 450° C. | 0.3 | 1.2 | 1.7 | 28.6 | 14.2 | 52.8 | — | 0.04 |
| Comp. Ex. 1 | 20:1:4 | 320 | Zn/$Al_2O_3$ | 0.3 | 0.07 | 31.0 | 23.3 | 2.4 | 42.2 | — | 0.02 |
| Comp. Ex. 2[c] | 20:1:4 | 300 | $Cr_2O_3$ 900° C. | 0.6 | 5.9 | 0.3 | 22.5 | 15.4 | 26.8 | 25.8 | 0.2 |
| Comp. Ex. 3[a] | 20:1:4 | 320 | $Cr_2O_3$ | 0.2 | 12.4 | 2.4 | 30.3 | 18.0 | 34.5 | — | 0.02 |

TABLE 1-continued

| EX. NO. | HF:1213:Cl₂ | T ° C. | Catalyst | 1215xc | 217ba | 226da | 216aa | 216ba | 215aa | 215bb | 214ab |
|---|---|---|---|---|---|---|---|---|---|---|---|
| Comp. Ex. 4ᵈ | 20:1:4 | 300 | Cr₂O₃ HSA | 0.9 | 0.1 | 11.7 | 25.9 | 1.6 | 59.2 | — | — |

Notes for TABLE I.
ᵃThe contact time was 15 seconds.
ᵇThe contact time was 5 seconds.
ᶜCatalyst prepared from pyrolyzed ammonium dichromate and calcined at 900° C. (see U.S. Pat. No. 5,036,036). Pre-treated with HF according to the general procedure.
ᵈHigh surface area chromium oxide obtained from a commercial source. Pre-treated with HF according to the general procedure.

| EX. NO. | H₂:216:HF | T ° C. | C₃H₈ | HFP | 236cb | 254eb/1225 | 227ea | 236ea | 236fa | 226ba | 226ea | 226da | 216ba |
|---|---|---|---|---|---|---|---|---|---|---|---|---|---|
| 12 | 2:1:0 | 125 | — | 0.2 | — | 0.1 | — | 0.8 | 13.8 | 0.1 | 1.5 | 36.9 | 46.4 |
| 13 | 2:1:0 | 175 | 0.3 | 0.2 | 0.1 | 0.3 | — | 9.1 | 27.3 | 1.0 | 11.6 | 26.8 | 23.2 |
| 14 | 2:1:0 | 225 | 0.5 | 1.1 | — | 0.9 | — | 27.8 | 40.0 | 1.4 | 8.7 | 13.3 | 5.7 |
| 15 | 2:1:0 | 250 | 1.7 | 2.0 | — | 0.9 | 0.1 | 31.9 | 42.2 | 1.4 | 6.0 | 10.0 | 2.6 |
| 16 | 2:1:2 | 250 | 0.3 | 2.2 | — | 0.7 | 0.2 | 35.4 | 43.3 | 1.4 | 4.2 | 9.7 | 1.8 |
| 17ᵃ | 2:1:2 | 300 | 3.6 | 1.9 | 5.5 | 2.5 | 20.3 | 3.7 | 39.9 | 0.9 | 2.4 | 9.4 | 4.2 |
| 18ᵇ | 2:1:2 | 350 | 2.0 | 2.9 | 0.6 | 1.6 | 27.2 | 2.0 | 34.8 | 0.5 | 2.0 | 10.0 | 7.9 |

ᵃThe product also contained 1.4 GC area % 245cb, 1.5% 1234, and 1.4% CH₄ and C₂H₆.
ᵇThe product also contained 0.4 GC area % 245cb, 0.9% 1234, and 2.0% CH₄ and C₂H₆.

What is claimed is:

1. A process for the manufacture of 1,1,1,3,3,3-hexafluoropropane and at least one compound selected from the group consisting of 1,1,1,2,3,3-hexafluoropropane and 1,1,1,2,3,3,3-heptafluoropropane, comprising:
   (a) reacting HF, Cl₂, and at least one halopropene of the formula CX₃CCl=CX₂, wherein each X is independently selected from the group consisting of F and Cl, to produce a product comprising CF₃CCl₂CF₃ and CF₃CClFCClF₂, wherein said CF₃CCl₂CF₃ and CF₃CClFCClF₂ are produced in the presence of a chlorofluorination catalyst comprising at least one composition selected from the group consisting of (i) compositions comprising ZnCr₂O₄ and crystalline α-chromium oxide, (ii) compositions comprising a zinc halide and α-chromium oxide and (iii) compositions of (i) or (ii) which have been treated with a fluorinating agent;
   (b) reacting CF₃CCl₂CF₃ and CF₃CClFCClF₂ produced in (a) with hydrogen, optionally in the presence of HF, to produce a product comprising CF₃CH₂CF₃ and at least one compound selected from the group consisting of CHF₂CHFCF₃, and CF₃CHFCF₃; and
   (c) recovering from the product produced in (b), CF₃CH₂CF₃ and at least one compound selected from the group consisting of CHF₂CHFCF₃ and CF₃CHFCF₃.

2. The process of claim 1 wherein the halopropene reactant is contacted with Cl₂ and HF in a pre-reactor.

3. The process of claim 1 wherein the halopropene reactant is contacted with HF in a pre-reactor.

4. The process of claim 1 wherein the reaction of (b) is conducted in a reaction zone which is unpacked or packed with a nickel alloy at a temperature of from about 350° C. to about 600° C.

5. The process of claim 1 wherein the reaction of (b) is conducted in a reaction zone containing a hydrogenation catalyst at a temperature of from about 100° C. to about 350° C.

6. The process of claim 1 wherein in (a) the catalyst is selected from the group consisting of (i) compositions comprising ZnCr₂O₄ and crystalline α-chromium oxide and (iii) compositions of (i) which have been treated with a fluorinating agent.

7. The process of claim 6 wherein the amount of zinc relative to the total of chromium and zinc in the catalyst composition is from about 1 atom % to about 25 atom %.

8. The process of claim 6 wherein the catalyst is selected from the group consisting of (i) compositions comprising ZnCr₂O₄ and crystalline α-chromium oxide wherein the ZnCr₂O₄ contains between about 10 atom percent and 67 atom percent of the chromium in the composition and at least about 70 atom percent of the zinc in the composition, and wherein at least about 90 atom percent of the chromium present as chromium oxide in the composition is present as ZnCr₂O₄ or crystalline α-chromium oxide and (iii) compositions of (i) which have been treated with a fluorinating agent.

9. The process of claim 1 wherein in (a) the catalyst is selected from the group consisting of (ii) compositions comprising a zinc halide and α-chromium oxide and (iii) compositions of (ii) which have been treated with a fluorinating agent.

10. The process of claim 9 wherein the amount of zinc relative to the total of chromium and zinc in the catalyst composition is from about 0.1 atom % to about 25 atom %.

11. The process of claim 9 wherein the catalyst is selected from the group consisting of (ii) compositions wherein a zinc halide is supported on a support comprising α-chromium oxide and (iii) compositions of (ii) which have been treated with a fluorinating agent; and wherein the amount of zinc relative to the total of chromium and zinc in the catalyst composition is from about 2 atom % to about 10 atom %.

* * * * *